United States Patent
Kim

(10) Patent No.: US 10,738,968 B2
(45) Date of Patent: Aug. 11, 2020

(54) OPTICAL MODULE

(71) Applicant: LG INNOTEK CO., LTD., Seoul (KR)

(72) Inventor: Ki Hyun Kim, Seoul (KR)

(73) Assignee: LG Innotek Co., Ltd., Seoul (KR)

( * ) Notice: Subject to any disclaimer, the term of this patent is extended or adjusted under 35 U.S.C. 154(b) by 167 days.

(21) Appl. No.: 16/087,371

(22) PCT Filed: Mar. 23, 2017

(86) PCT No.: PCT/KR2017/003143
§ 371 (c)(1),
(2) Date: Sep. 21, 2018

(87) PCT Pub. No.: WO2017/164672
PCT Pub. Date: Sep. 28, 2017

(65) Prior Publication Data
US 2020/0124248 A1 Apr. 23, 2020

(30) Foreign Application Priority Data
Mar. 23, 2016 (KR) .................. 10-2016-0034922

(51) Int. Cl.
F21V 5/04 (2006.01)
A61L 2/10 (2006.01)
(Continued)

(52) U.S. Cl.
CPC .............. F21V 5/04 (2013.01); A61L 2/10 (2013.01); A61L 2/26 (2013.01); G02B 3/04 (2013.01);
(Continued)

(58) Field of Classification Search
None
See application file for complete search history.

(56) References Cited

U.S. PATENT DOCUMENTS 6,504,301 B1 * 1/2003 Lowery ............... F21V 9/45
313/512
7,207,697 B2 * 4/2007 Shoji ................ F21V 5/045
362/187
(Continued)

FOREIGN PATENT DOCUMENTS

DE 202014003077 U1 * 4/2014 ......... G02B 19/0028
KR 10-2007-0036900 A 4/2007
(Continued)

OTHER PUBLICATIONS

International Search Report (PCT/ISA/210) issued in PCT/KR2017/003143, dated May 23, 2017.

Primary Examiner — J. E. Schoenholtz
(74) Attorney, Agent, or Firm — Birch, Stewart, Kolasch & Birch, LLP

(57) ABSTRACT

An optical module disclosed in an embodiment includes: a body including a recess recessed at a predetermined depth from an upper surface thereof and a side surface having an outwardly concave curved surface at a periphery of the recess; a light emitting module having a light emitting diode at a lower portion of the recess of the body; and an optical lens including an incidence portion disposed on the body and a lens portion having an aspherical shape on the incidence portion, and wherein an upper portion of the recess has a maximum first diameter, a lower portion of the lens portion has a maximum second diameter, and the second diameter is smaller than the first diameter.

20 Claims, 8 Drawing Sheets

(51) Int. Cl.
*A61L 2/26* (2006.01)
*G02B 3/04* (2006.01)
*H01L 33/58* (2010.01)
*F21Y 115/10* (2016.01)

(52) U.S. Cl.
CPC .......... *H01L 33/58* (2013.01); *A61L 2202/11* (2013.01); *F21Y 2115/10* (2016.08)

(56) References Cited

U.S. PATENT DOCUMENTS

| | | | | |
|---|---|---|---|---|
| 8,485,692 B2 * | 7/2013 | Li | ................... | G02B 19/0066 |
| | | | | 362/308 |
| 9,488,331 B2 * | 11/2016 | Sharrah | ................ | F21V 7/0091 |
| 10,254,521 B2 * | 4/2019 | Sun | ................... | F21V 5/007 |
| 2013/0032828 A1 * | 2/2013 | Hsu | ................... | H01L 25/0753 |
| | | | | 257/88 |
| 2014/0117391 A1 | 5/2014 | Ha et al. | | |

FOREIGN PATENT DOCUMENTS

| | | | |
|---|---|---|---|
| KR | 10-0855356 B1 | 9/2008 | |
| KR | 10-2014-0008670 A | 1/2014 | |
| KR | 10-2014-0049274 A | 4/2014 | |
| KR | 20140049274 A * | 4/2014 | ............ H01L 33/58 |
| KR | 10-2014-0055605 A | 5/2014 | |
| KR | 10-2014-0056571 A | 5/2014 | |
| KR | 10-2015-0130887 A | 11/2015 | |

\* cited by examiner

OPTICAL MODULE

CROSS REFERENCE TO RELATED APPLICATIONS

This application is the National Phase of PCT International Application No. PCT/KR2017/003143, filed on Mar. 23, 2017, which claims priority under 35 U.S.C. 119(a) to Patent Application Ser. No. 10-2016-0034922, filed in the Republic of Korea on Mar. 23, 2016, all of which are hereby expressly incorporated by reference into the present application.

TECHNICAL FIELD

An embodiment relates to an optical module.
An embodiment relates to an optical module for narrow angle.

BACKGROUND ART

A light emitting diode (LED) may constitute a light emitting source using a compound semiconductor material such as GaAs-based, AlGaAs-based, GaN-based, InGaN-based, and InGaAlP-based semiconductor materials.

Such a LED is packaged and used as a light emitting device which emits light of various colors. The light emitting device is used as a light source in various fields, such as a lighting indicator for displaying a color, a character indicator, and an image indicator.

Particularly, in case of an ultraviolet LED (UV LED), a short wavelength may be used for sterilization and purification, and a long wavelength may be used for an exposure apparatus or a curing apparatus. Since a luminous intensity of a light emitting device having such a UV LED is low, it is required to improve the luminous intensity.

DISCLOSURE

Technical Problem

An embodiment provides an optical module having a light emitting diode emitting an ultraviolet wavelength.
An embodiment provides an optical module for narrow angle having an ultraviolet light emitting diode.
An embodiment provides an optical module for exposure or narrow angle having a beam spread angle of 15 degrees or less.

Technical Solution

An optical module according to an embodiment comprises: a body including a concave recess and a side surface having an outwardly concave curved surface at a periphery of the recess; a light emitting module having a light emitting diode at a lower portion of the recess of the body; and an optical lens including an incidence portion disposed on the body and a lens portion having a convex curved surface on the incidence portion, wherein the incidence portion is disposed on an upper surface of the body and on the recess, the incidence portion includes a first region overlapped with the upper surface of the body in a vertical direction and a second region overlapped with an upper portion of the recess in the vertical direction along an outer periphery of the lens portion, the lens portion is overlapped with the recess in the vertical direction, the upper portion of the recess has a maximum first diameter, a lower portion of the lens portion has a maximum second diameter, the second diameter is smaller than the first diameter, the lower portion of the recess has a third diameter smaller than the second diameter, and an upper surface of the light emitting diode is disposed lower than a horizontal straight line connecting a lower end of curved surface of the recess.

According to the embodiment, wherein the body includes a receiving portion in which the light emitting module is disposed and a bottom of the recess is opened, the light emitting module includes a circuit board disposed on a bottom of the receiving portion and electrically connected to the light emitting diode, and a bottom center of the receiving portion is aligned with a center of the lens portion.

According to the embodiment, wherein the lens portion includes an aspherical shape, the second diameter is 80% or more of the first diameter, and an area of a lower surface of the second region in the incidence portion is smaller than that of a lower surface of the first region.

According to the embodiment, wherein a height of the optical lens is smaller than a depth of the recess, a ratio of the first diameter and the second diameter is in a range of 1: 0.81 to 1: 0.91, and the incidence portion of the optical lens has a flat incidence surface, and a beam spread angle of light emitted from the optical lens is 15 degrees or less.

According to the embodiment, wherein first light emitted from the light emitting diode is directly incident on the lens portion at a first incidence angle with respect to an optical axis, and is emitted at a first exit angle through the lens portion, and second light emitted from the light emitting diode is reflected at a side surface of the recess at a second incidence angle with respect to the optical axis, and is emitted at a second exit angle through the incidence portion disposed at an outside of the lens portion, wherein the first incidence angle is 35 degrees or less with respect to the optical axis, the second incidence angle is greater than 35 degrees with respect to the optical axis, and the first and second exit angles include 15 degrees or less with respect to the optical axis or a vertical axis.

According to the embodiment, wherein first light emitted from the light emitting diode is directly incident on the lens portion at a first incidence angle with respect to an optical axis, and is emitted at a first exit angle through the lens portion, and second light emitted from the light emitting diode is reflected at a side surface of the recess at a second incidence angle with respect to the optical axis, and is emitted at a second exit angle through the incidence portion disposed at an outside of the lens portion, wherein a ratio of the first incidence angle and the first exit angle is 1.7 or less, and a ratio of the second incidence angle and the second exit angle is 0.375 or less.

According to the embodiment, wherein the body includes a ceramic material or an aluminum material, the recess has a circular shape in top view, and the diameter of the recess gradually decreases toward the light emitting diode.

According to the embodiment, wherein the curved surface of the recess has a radius of curvature of 1.5 mm or less, and a lower surface of the incidence portion includes a flat horizontal surface, and an area of the lower surface of the incidence portion is larger than that of an upper surface of the recess.

According to the embodiment, wherein the light emitting diode emits light of an ultraviolet wavelength, the recess has a circular shape in top view, the diameter of the recess gradually decreases toward the light emitting diode, and a beam spread angle of light emitted from the optical lens is 15 degrees or less.

According to the embodiment, wherein the light emitting diode emits light of an ultraviolet wavelength, the recess has a circular shape in top view, the diameter of the recess gradually decreases toward the light emitting diode, a lower surface of the circuit board is disposed in the same horizontal plane as a lower surface of the body and disposed in the receiving portion, the circuit board includes a ceramic material, and a width of the circuit board is smaller than that of the receiving portion.

Advantageous Effects

An embodiment may provide an optical beam spread angle of an optical module with a narrow angle of 15 degrees or less.

An embodiment may improve the reliability of an exposure optical apparatus.

An embodiment may reduce the number of ultraviolet light emitting diodes disposed in an optical module.

In an embodiment, it is possible to improve the reliability in an exposure apparatus by providing an exposure optical module having a narrower beam spread angle than a Lambertian luminous intensity distribution.

MODES OF THE INVENTION

Figure 1:
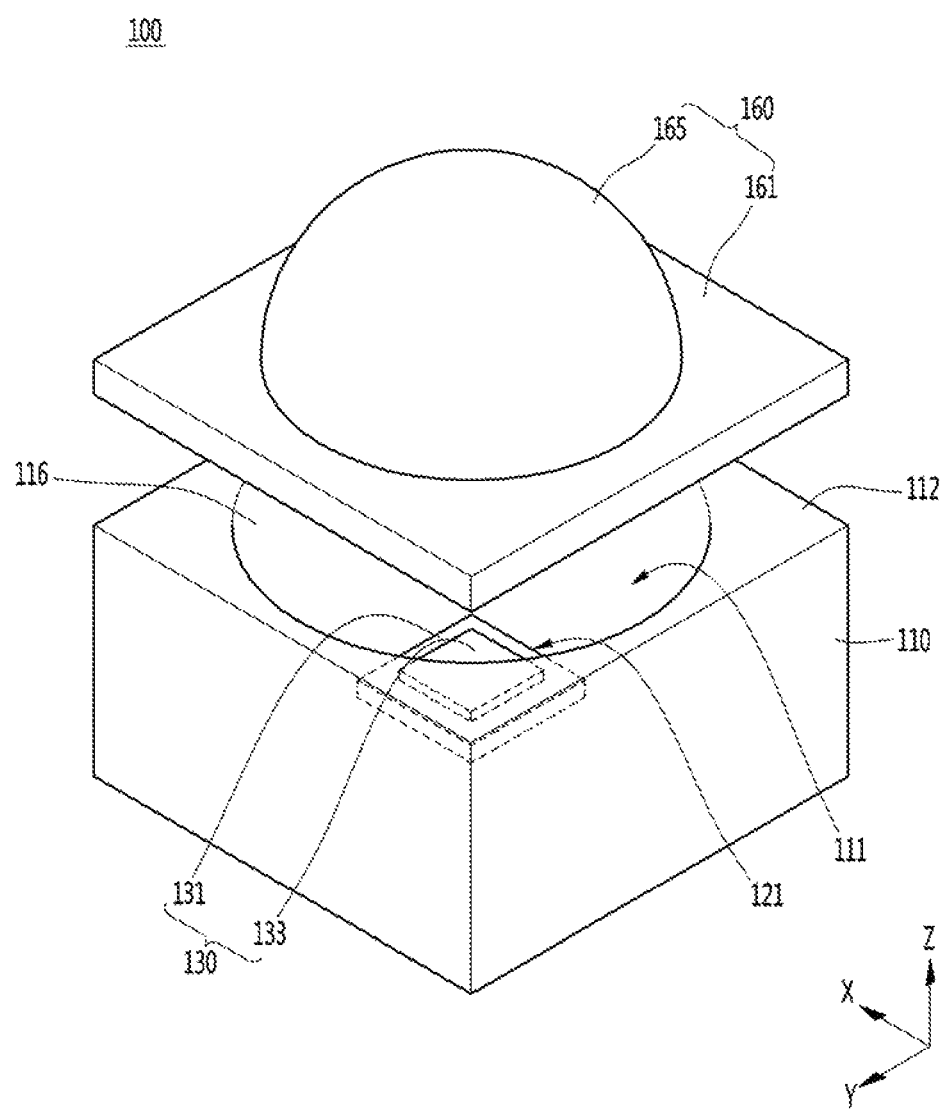
FIG. 1 is a perspective view of a light emitting module according to an embodiment.

Hereinafter, exemplary embodiments of the present invention that are easily performed by those skilled in the art will be described in detail with reference to the accompanying drawings. However, the present invention may be implemented in various different forms and is not limited to the embodiments described herein.

In the following description, when there is an expression that some portion "includes" some structural elements, this means that some portion does not exclude another structural element, but may further include another structural element unless stated to the contrary. Further, structures and elements which do not relate to the detail description are not shown in the drawings to clearly describe the present invention, thicknesses may be exaggerated to clearly explain various layers and regions, and similar elements in the following description are designated by similar reference numerals.

In the description of the embodiment, when a portion of a layer, a film, a region, a plate or the like is referred to as being "on" another portion, it can be "directly formed on" another portion, or a third portion can be interposed between the portions. Otherwise, when a portion is "directly formed on" another portion, it means that there is no third portion between the portions.

Lighting Module

Figure 2:
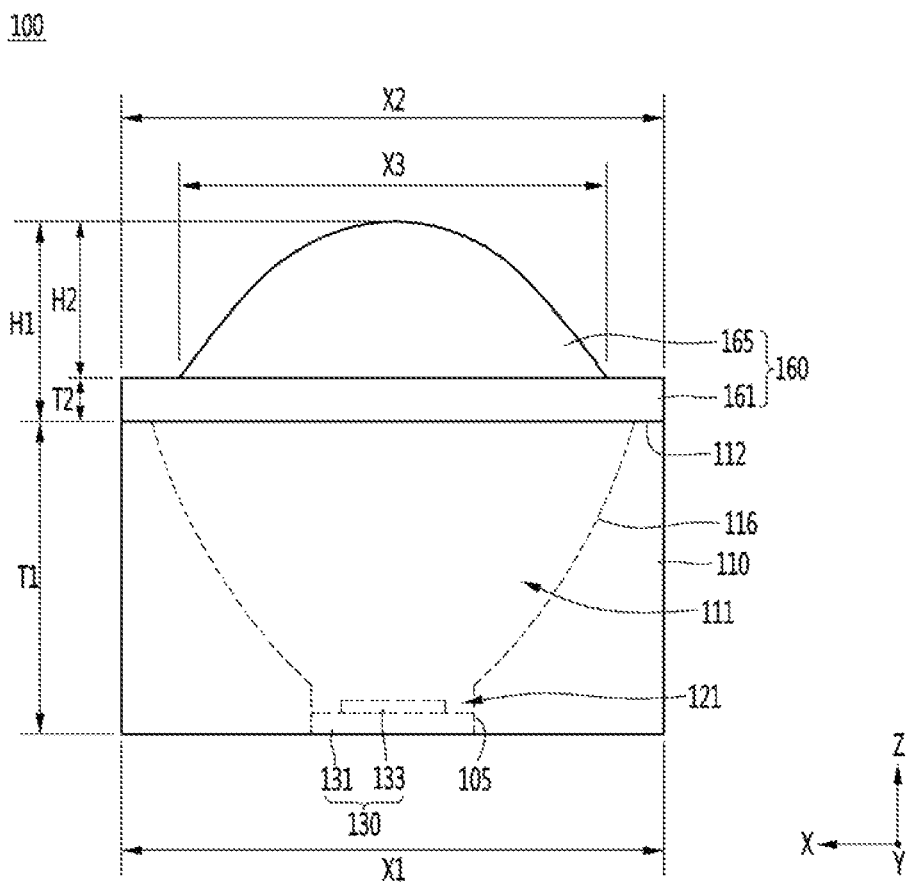
FIG. 2 is a coupled side view of an optical module of FIG. 1.
Figure 3:
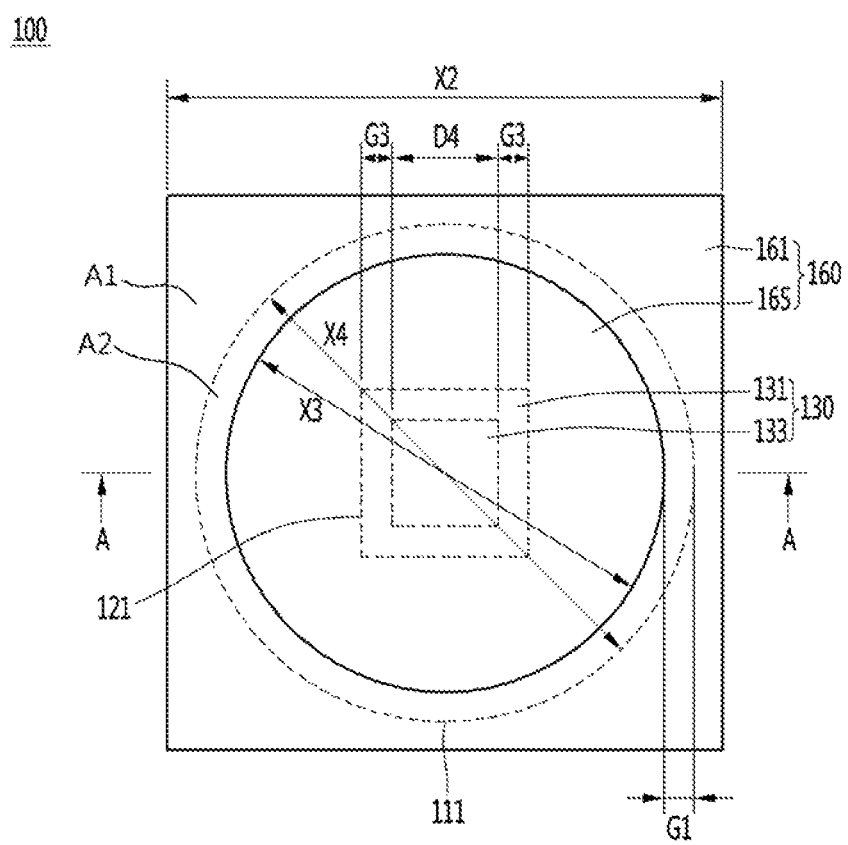
FIG. 3 is a plan view of the optical module of FIG. 2.
Figure 4:
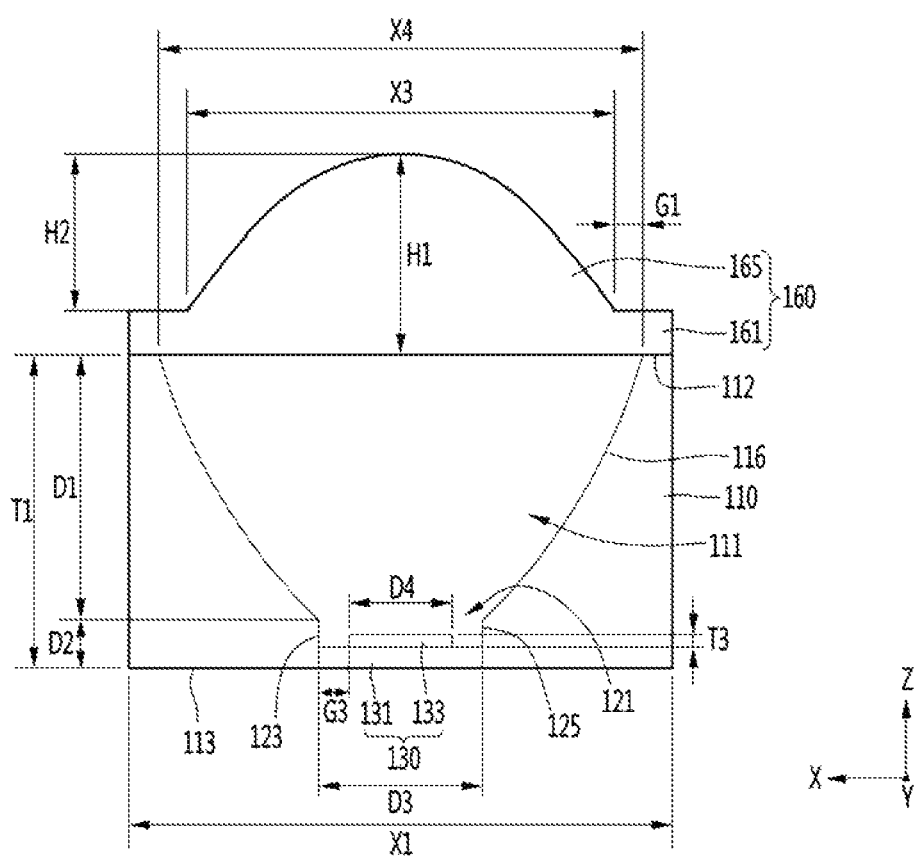
FIG. 4 is a cross-sectional view taken along line A-A of the optical module of FIG. 3.
Figure 5:
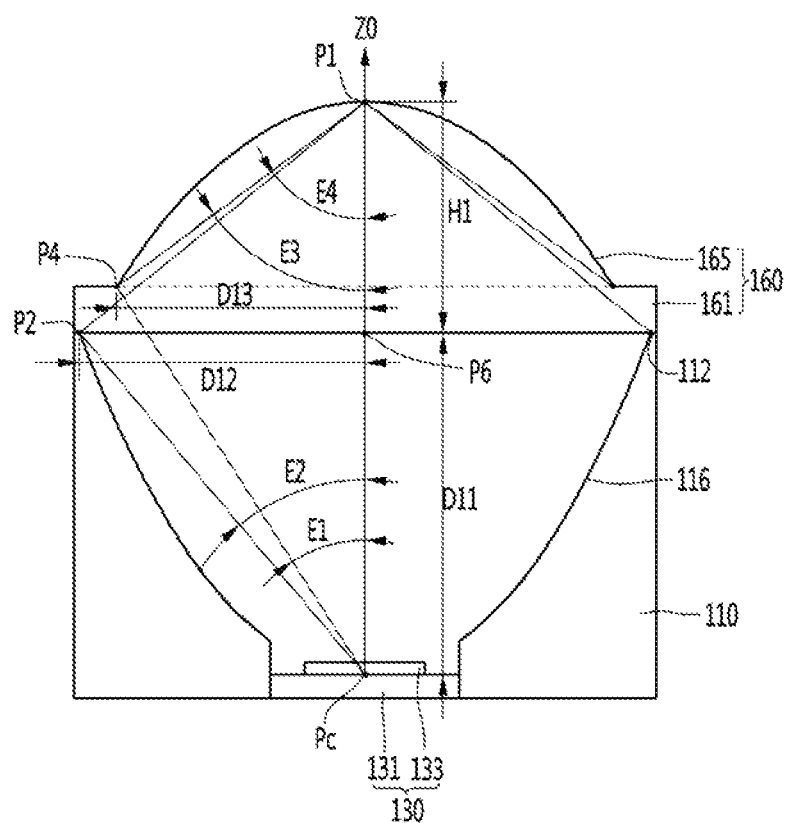
FIG. 5 is a view for describing a structure of a recess of a body and an optical lens in the optical module of FIG. 4.
Figure 6:
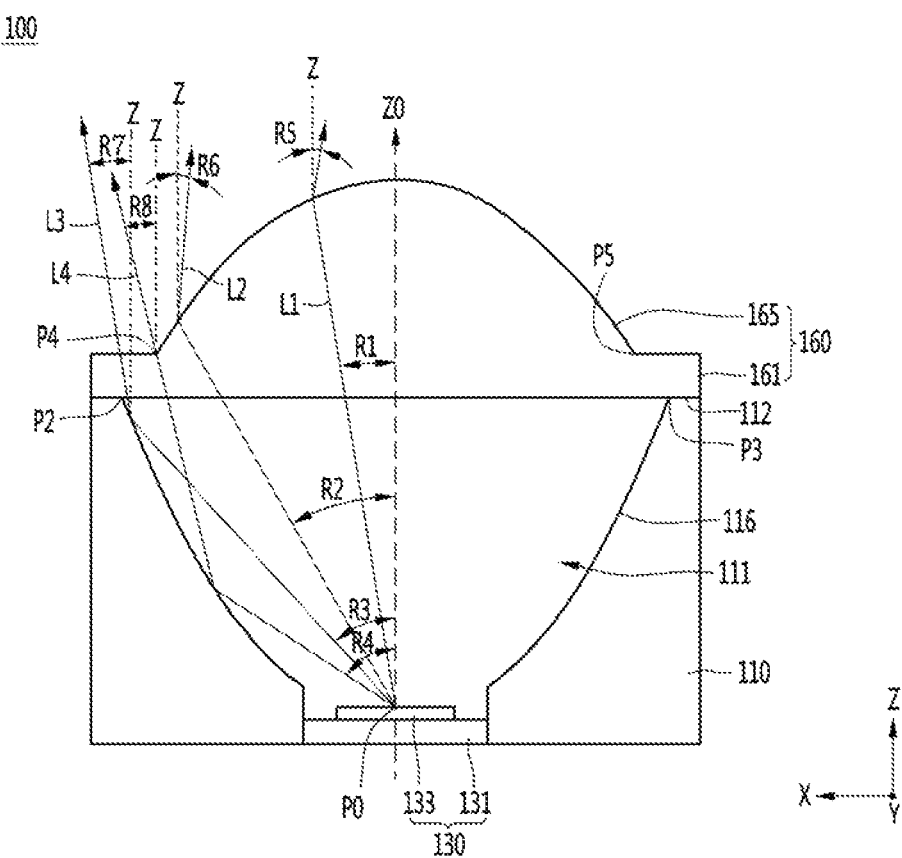
FIG. 6 is a view for describing an optical path in the optical module of FIG. 4.

FIG. 1 is a perspective view of a light emitting module according to an embodiment, FIG. 2 is a coupled side view of an optical module of FIG. 1, FIG. 3 is a plan view of the optical module of FIG. 2, FIG. 4 is a cross-sectional view taken along line A-A of the optical module of FIG. 3, FIG. 5 is a view for describing a structure of a recess of a reflector and an optical lens in the optical module of FIG. 4, and FIG. 6 is a view for describing an optical path in the optical module of FIG. 4.

Referring to FIGS. 1 to 6, an optical module 100 includes a body 110 having a recess 111, a light emitting module 130 disposed at a bottom of the recess 111, and an optical lens 160 disposed on the body 110.

The body 110 may be a reflector formed of a reflective material. The body 110 may be formed of a metal material, for example an aluminum material. The body 110 may be formed of a metal material, or may be plated with an aluminum material on a surface thereof. The body 110 may be formed of a material having 100% aluminum. The body 110 may optionally include a metal, for example, aluminum (Al), platinum (Pt), titanium (Ti), copper (Cu), nickel (Ni), gold (Au), and tantalum (Ta), and may be formed as a single layer or multiple layers. The body 110 may be formed of a metal having a reflectance of 80% or more of a wavelength emitted from the light emitting module 130. The body 110 may include an insulating material or a conductive material. The body 110 includes a ceramic material, and a metal layer, for example, an aluminum material, may be formed on a side surface 116 of the recess 111.

As shown in FIG. 2 and FIG. 3, a top view shape of the body 110 may be a polygonal shape, for example, a rectangular shape, and as another example, may be a circular shape. The outer shape of the body 110 may be a polyhedron shape, but is not limited thereto. A horizontal or vertical length X1 at an upper surface 112 or a bottom surface 113 of the body 110 may be the same as or different from each other, but is not limited thereto. An area of the bottom surface 113 of the body 110 may be equal to or larger than that of the upper surface 112 thereof. A height T1 of the body 110 may be smaller than the horizontal or vertical length X1 of the body 110.

In the body 110, a recess 111 having an open upper portion and a receiving portion 121 disposed at a lower portion of the recess 111 are disposed, and the light emitting module 130 is disposed at the receiving portion 121. The recess 111 is recessed at a predetermined depth from the upper surface 112 of the body 110 and connected to the receiving portion 121, and the receiving portion 121 may be a region in which a lower portion of the body 110 is opened.

The recess 111 may have a shape that gradually narrows downward, for example, a hemispherical shape or a container shape. The recess 111 may be formed in a rotationally symmetric shape or an axisymmetric shape with reference to an optical axis perpendicular to a bottom center thereof. Inside of the recess 111 may be a vacant space.

A shape of the upper portion of the recess 111 may be a circular shape having a maximum first diameter X4, and the bottom shape may be a polygonal shape or a circular shape. The recess 111 has a shape in which the diameter gradually decreases as descending downward and may be connected to the receiving portion 121 at a lower end of the recess 111. The side surface 116 of the recess 111 may be a reflecting surface, and the reflecting surface may be formed of a metal reflecting material different from the body 110 or may be formed of a material of the body 110. The side surface 116 of the recess 111 may include an outwardly concave curved surface, and the curved surface may be a concave surface that is outwardly curved than a straight line connecting an upper end and the lower end of the recess 111. The curved surface may be formed in a parabolic shape or a quadratic curve shape between the upper end and the lower end of the recess 111. Here, the upper end of the recess 111 may be a boundary point with an upper end of the body 110, and the lower end may be a boundary point with the receiving portion 121. When the side surface 116 of the recess 111 is a curved surface, a radius of curvature may be 1.5 mm or less, for example, in a range of 1.2 to 1.5 mm, and when the radius of curvature is out of the above range, reflection efficiency of light may be reduced. When the top view shape of the recess 111 is a circular shape, the diameter thereof may decrease toward a light emitting diode 133.

A depth D1 of the recess 111 may be larger than a height H1 of the optical lens 160, and for example, the depth D1 may be 1.4 times or more, for example, in a range of 1.4 to 1.8 times the height H1. The depth D1 may be 3.5 mm or more, for example, in a range of 3.5 to 4.2 mm. The recess 111 having the depth D1 may sufficiently diffuse light. An area of a lower surface of an incidence portion 161 of the optical lens 160 may be larger than that of an upper surface of the recess 111.

A top view shape of the receiving portion 121 may be a polygonal shape or a circular shape, and may have a predetermined height D2 from the bottom surface 113 of the body 110. A width D3 of the receiving portion 121 may be in a range of 1.8 to 2.5 mm, and the width may be changed according to a width D4 of the light emitting diode 133. The height D2 of the receiving portion 121 is disposed to be greater than a thickness of the light emitting module 130, and an upper end of the receiving portion 121 or a boundary point thereof with the recess 111 may be disposed above an upper surface of the light emitting diode 133. The upper surface of the light emitting diode 133 may be disposed lower than a straight line connecting the lower end of the concave curved surface of the recess 111. The receiving portion 121 may vary according to a size of the light emitting module 130, and may be formed such that light emitted from the light emitting module 130 is reflected through the side surface 116 of the recess 111 without loss in the receiving portion 121.

The light emitting module 130 includes a circuit board 131 and the light emitting diode 133 on the circuit board 131. The circuit board 131 may include a resin-based substrate, a ceramic-based substrate, or a metal-based substrate. The circuit board 131 may be a rigid substrate or a flexible substrate. The circuit board 131 may have a circuit pattern and may supply power to the light emitting diode 133. A width of the circuit board 131 may be less than or equal to the width of the receiving portion 121. When the width of the circuit board 131 is less than or equal to the width of the receiving portion 121, the circuit board 131 may be in close contact with a side wall of the receiving portion 121. When the width of the circuit board 131 is greater than the width of the receiving portion 121, the circuit board 131 may extend from under the receiving portion 121 to a lower surface of the body 110. A lower surface of the circuit board 131 may be disposed in the same horizontal plane as the lower surface of the body 110.

The light emitting diode 133 may include a peak wavelength which is optional in a wavelength range from ultraviolet rays to visible light. The light emitting diode 133 may emit an ultraviolet wavelength, for example, and may be applied to an exposure apparatus, a sterilization apparatus, or a curing apparatus.

The light emitting diode 133 may be formed of a compound semiconductor of an element of Group II and Group VI or a compound semiconductor of an element of Group III and Group V. For example, the light emitting diode 133 may be an ultraviolet light emitting diode (LED) chip, and may be an LED chip having a wavelength in a range from 100 nm to 400 nm. For example, the light emitting diode 133 may selectively include a semiconductor element manufactured by using a compound semiconductor, such as AlInGaN, InGaN, AlGaN, GaN, GaAs, InGaP, AlInGaP, InP, or InGaAs series. The light emitting diode 133 may include an N-type semiconductor layer, a P-type semiconductor layer, and an active layer. The active layer may be implemented with compound semiconductors in pairs, such as InGaN/GaN, InGaN/AlGaN, InGaN/InGaN, GaN/AlGaN, InAlGaN/InAlGaN, AlGaAs/GaAs, InGaAs/GaAs, InGaP/GaP, AlInGaP/InGaP, and InP/GaAs. The light emitting diode 133 may be a horizontal type chip or a vertical type chip, and may be disposed on the circuit board 131 and electrically connected using a connection member such as a wire and disposed in a flip chip type, but is not limited thereto.

A thickness T3 of the light emitting diode 133 may be in the range of 0.13 mm±0.03 mm. The width D4 of the light emitting diode 133 may be a length of one side in the range of 1.3 mm±0.4 mm, but is not limited thereto. A distance G3 between the light emitting diode 133 and the side wall of the receiving portion 121 may be less than 0.5 mm, for example, in a range of 0.32 mm to 0.42 mm. Light emitted from the light emitting diode 133 is reflected and re-reflected by the side wall of the receiving portion 121 since the light emitting diode 133 is spaced apart from the side wall of the receiving portion 121 by the distance G3, thereby preventing loss of the light. A beam spread angle of the light emitting diode 133 may be 110 degrees or more, for example, in a range of 110 degrees to 130 degrees, and the width D3 of the receiving portion 121 may vary according to a distribution of the beam spread angle of the light emitting diode 133, but is not limited thereto.

As shown in FIGS. 2 to 4, the optical lens 160 is disposed on the body 110, and refracts and emits the light emitted from the light emitting diode 133. The optical lens 160 may be adhered to an upper surface of the body 110 with an adhesive (not shown). An incidence surface of the optical lens 160 may be formed in a flat horizontal surface or an upwardly convex surface. An emission surface of the optical lens 160 may include a convex lens shape, and the convex lens shape may refract and emit light incident on the incident surface. Here, the optical lens 160 may have a thickness H1 smaller than the height T1 of the body 110 and may have a thickness of 3 mm or less, for example, in a range of 2 mm to 3 mm. When the thickness H1 of the optical lens 160 is larger than the above range, the size of the optical module 100 increases, and when the thickness H1 is smaller than the above range, the optical loss may increase. The horizontal and vertical lengths X2 of the optical lens 160 may be the same as or different from each other and may be the same as or different from the horizontal and vertical lengths X1 of the body 110. The horizontal and vertical lengths X2 of the optical lens 160 may be 8 mm or less, for example, in a range of 6.5 mm to 8 mm, and may vary according to a size of the body 110. The optical lens 160 may be formed of a transparent material, for example, a glass material. The optical lens 160 may be formed of, for example, a borosilicate-based glass material.

The optical lens 160 includes an incidence portion 161 and a lens portion 165 on the incidence portion 161. The incidence portion 161 is disposed on the upper surface 112 of the body 110, and the lens portion 165 has a lens shape convexly protruding from the incidence portion 161. The incidence portion 161 is a flange and is disposed at a thickness T2 of 30% or less, for example, 10% to 30% of the thickness H1 of the optical lens 160, and transmits incident light and supports the optical lens 160 on the body 110. A lower surface of the incidence portion 161 may include a flat incidence surface.

The incidence portion 161 includes a first region (A1 in FIG. 3) overlapped with the upper surface of the body 110 in a vertical direction and a second region (A2 in FIG. 3) overlapped with the upper surface of the recess 111 in a vertical direction along an outer periphery of the lens portion 165. An area of a lower surface of the second region A2 in the incidence portion 161 may be smaller than that of a lower surface of the first region A1. Accordingly, it is possible to support the optical lens 160 through the first region Al and adjust an amount of leakage light traveling to a path other than the lens portion 165 through the second region A2.

The lens portion 165 of the optical lens 160 is formed in a convex lens shape convex upward from the incidence portion 161, and the surface thereof may be formed in a curved surface or aspherical shape. A center of the lens portion 165 may be aligned with the bottom center of the recess 111. A thickness H2 of the lens portion 165 may have a range of 70% to 90% of the thickness H1 of the optical lens 160, and a radius of curvature thereof may be 2 mm or less, for example, in a range of 1.80 mm to 2 mm. The thickness H2 and the radius of curvature of the lens portion 165 may vary according to a size of the light emitting diode 133.

The lens portion 165 may have a second diameter X3 which is the maximum diameter of a lower portion. The second diameter X3 may be smaller than the first diameter X4 and may be less than 6 mm, for example, in a range of 5.32 to 5.42 mm. When the second diameter X3 of the lens portion 165 is smaller than the above range, the beam spread angle of light emitted through the incidence portion 161 disposed on the outer periphery of the lens portion 165 may be increased, and when the second diameter X3 of the lens portion 165 is larger than the above range, the light is totally reflected inside the lens portion 165, thereby occurring light loss. The second diameter X3 may be smaller than the first diameter X4 and may be 80% or more thereof. The ratio of the first diameter X4 and the second diameter X3 may be in a range of 1:0.81 to 1:0.91, and the difference between the first diameter X4 and the second diameter X3 may have a range greater than 0.7 mm and less than 1 mm, for example, a range of 0.76 to 0.86 mm. When a diameter of the lower portion of the recess 111 is a third diameter (e.g., D3), the second diameter X3 may be smaller than the first diameter and may be larger than the third diameter D3. An addition, when a diameter at a half point of the height of the recess 111 is defined as a fourth diameter, the fourth diameter may be smaller than the second diameter X3. The outer region of the lens portion 165 having the second diameter X3 may be formed at a region between a path of light reflected at the side surface 116 of the recess 111 and a path of light out of the side surface 116 of the recess 111.

Figure 9:
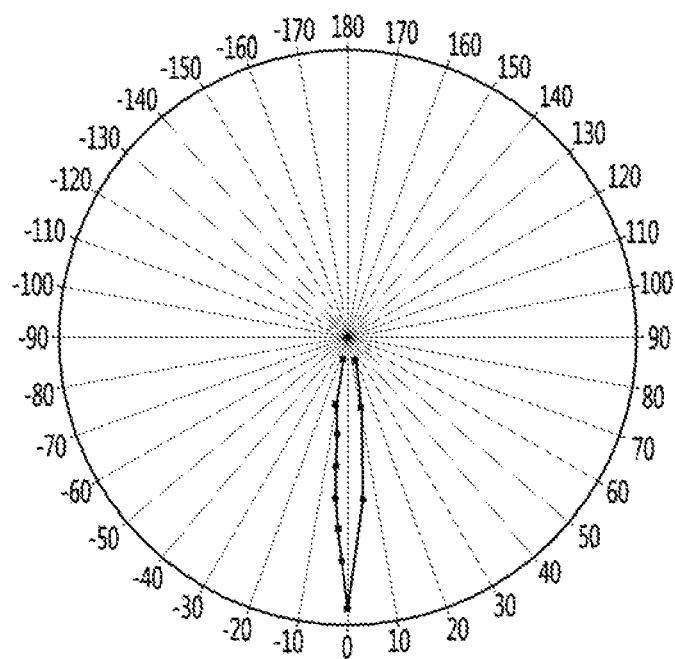
FIG. 9 is a view illustrating a beam spread angle distribution of light emitted from an optical module according to an embodiment.

An area of the lower portion (excluding the incidence portion) of the lens portion 165 may be smaller than an area of the upper surface of the recess 111. The optical lens 160 may have a beam spread angle distribution for a narrow angle by using light that is incident on and emitted from the lens portion 165 and light that is incident on and reflected outside the incidence portion 161 by a difference G1 between the first and second diameters X4 and X3. For example, the lens portion 165 and the incidence portion 161 may be provided with a beam spread angle distribution of 15 degrees or less by using incident light. The optical lens 160 may emit light having a beam spread angle in the range of 10% to 14% with respect to a beam spread angle of the light emitting diode 133. The optical module 100 may provide a light beam spread angle distribution of 15 degrees or less as shown in FIG. 9. The optical module having the beam spread angle distribution may be applied to an apparatus that condenses light in a specific area, such as an exposure apparatus. In addition, the number of light emitting diodes 133 under the recess 111 may be reduced in the optical module.

Referring to FIG. 5, a bottom center Pc of the light emitting diode 133 and a peak point P1 of the lens portion 165 of the optical lens 160 may be aligned on an optical axis Z0. The bottom center Pc of the light emitting diode 133 may be a center of an upper surface of the circuit board 131. A straight line connecting the bottom center Pc of the light emitting diode 133 and an upper end P2 of the side surface 116 of the recess 111 is a second angle E2 with respect to the optical axis Z0, and a straight line connecting the bottom center Pc of the light emitting diode 133 and an outer low point P4 of the lens portion 165 of the optical lens 160 may be a first angle E1 with respect to the optical axis Z0. The second angle E2 is disposed to be larger than the first angle E1 so that some light may be emitted through a region between the first and second angles E1 and E2. A difference between the first and second angles E1 and E2 may be in the range of 7.3 ±0.7 degrees. The first angle E1 may be disposed at an angle of 35 degrees or less, for example, in a range of 31 to 35 degrees. Here, a distance D11 from the bottom center Pc of the light emitting diode 133 or the upper surface of the circuit board 131 to the incidence surface of the optical lens 160 may be greater than a radius D12 of the first diameter of the recess 111, and the radius D12 of the first diameter may be greater than the thickness H1 of the optical lens 160. Here, a ratio of the radius D12 of the first diameter to the radius D13 of the lens portion 165 may have a ratio of 1: 0.81 to 1: 0.91. The light incident on the lens portion 165 and the light reflected through the incidence portion 161 may be transmitted by a difference in the ratio of the radius D12 of the first diameter to the radius D13 of the lens portion 165. In the present invention, by controlling the paths of the reflected light and the transmitted light by a difference in a ratio of the size of the incidence surface of the optical lens 160, the diameter of the lower portion of the lens portion 165, and the diameter of the upper portion of the recess 111, a distribution of light traveling to the surface of the lens portion 165 may have a narrow beam spread angle.

A straight line connecting the peak point P1 of the optical lens 160 and the outer low point P4 of the lens portion 165 has a third angle E3 with respect to the optical axis Z0, and a straight line connecting the peak point P1 of the optical lens 160 and the upper end P2 of the side surface of the recess 111 may be disposed at a fourth angle E4 with respect to the optical axis Z0. The third angle E3 may be greater than the fourth angle E4, and a difference between the third and fourth angles E3 and E4 may be 2 degrees or more, for example, in a range of 2 to 4 degrees, and light incident on the lens portion 165 may be distinguished from light which is not incident thereon by the difference. The third angle E3 may be in a range of 50 to 52 degrees. The ratio of the third and fourth angles E3 and E4 may have a range of 1.02:1 or more, for example, 1.02: 1 to 1.2: 1. The third angle E3 may vary according to a size of the recess 111 and the radius of curvature of the lens portion 165.

The optical lens 160 may provide a light distribution having a narrow angle, for example, a beam spread angle of 15 degrees or less by refracting light incident on the lens portion 165 through the recess 111. The optical lens 160 may provide a beam spread angle of 15 degrees or less by emitting light transmitted through the outer side incidence portion 161 of the lens portion 165 at 15 degrees or less.

Referring to FIG. 6, on the basis of the optical path, pieces of light L1 and L2 traveling directly to the lens portion 165 of the optical lens 160 at first incidence angles R1 and R2 with respect to the optical axis Z0 among the light emitted from the light emitting diode 133, are refracted by the lens portion 165 and then emitted at first exit angles R5 and R6 of 15 degrees or less with respect to a vertical axis Z. The first incidence angles R1 and R2 are angles between the pieces of light L1 and L2, emitted with respect to a center P0 of the upper surface of the light emitting diode 133, and the optical axis Z0. The maximum angle of the first incidence angles R1 and R2 may be an angle at which the light emitted from the light emitting diode 133 is incident on the outer low points P4 and P5 of the lens portion 165. Here, the maximum angle of the first incidence angles R1 and R2 may be emitted at an angle of 35 degrees or less with respect to the optical axis Z0. When the first incidence angles R1 and R2, for example, is in a range of 10 to 35 degrees, ratios (R5/R1 and R6/R2) of the first exit angles R5 and R6 and the first incidence angles R1 and R2 may be emitted to the lens portion 165 with a ratio of 1.7 or less. When the ratios (R5/R1 and R6/R2) of the first exit angles R5 and R6 and the first incidence angles R1 and R2 exceed the above range, there is a problem that has a beam spread angle exceeding 15 degrees.

Among the light emitted from the light emitting diode 133, some pieces of light L3 and L4 traveling to the side surface 116 of the recess 111 at second incidence angles R3 and R4 with respect to the optical axis Z0, are reflected at the side surface 116 of the recess 111 and emitted through between the upper ends P2 and P3 of a side surface of the recess 111 and an outer point P4 of the lens portion 165. At this point, the second incidence angles R3 and R4 travels at an angle exceeding 35 degrees with respect to the optical axis Z0. The pieces of light L3 and L4 emitted at the second incidence angles R3 and R4 are refracted through the incidence portion 161 and emitted at second exit angles R7 and R8, and the second exit angles R7 and R8 travel at 15 degrees or less with respect to the vertical axis Z. The second incidence angles R3 and R4 are angles between the pieces of light L3 and L4 emitted with respect to the center P0 of the upper surface of the light emitting diode 133 and the optical axis Z0. Here, the pieces of light L3 and L4 emitted to the outer side incidence portion 161 of the lens portion 165 of the optical lens 160 have the second incidence angles R3 and R4 exceeding 35 degrees with respect to the optical axis Z0, and the second exit angles R7 and R8 of 15 degrees or less with respect to the vertical axis Z. In the case of light traveling at the second incidence angles R3 and R4, for example, the pieces of light L3 and L4 having a range of 36 to 65 degrees with respect to the optical axis Z0, ratios (R7/R3 and R8/R4) of the second exit angles R7 and R8 and the second incidence angles R3 and R4 may be a ratio of 0.375 or less. When the ratios (R7/R3 and R8/R4) of the second exit angles R7 and R8 and the second incidence angles R3 and R4 exceed the above range, there is a problem that has a beam spread angle exceeding 15 degrees.

Here, light out of a beam spread angle among light emitted through the light emitting diode 133, for example, pieces of light exceeding 65 degrees with respect to the optical axis Z0 (for example, when a beam spread angle is 130 degrees) are pieces of light out of a beam spread angle distribution of light, and influence on light distribution may not be significant.

Among the light emitted from the light emitting diode 133, pieces of light L1 and L2 of 35 degrees or less with respect to the optical axis Z0 travel to the lens portion 165 of the optical lens 160, and are emitted outside through the incidence portion 161 of the optical lens 160 in a period of more than 35 degrees and 60 degrees or less. The optical module 100 may be provided as a narrow angle module having the beam spread angle as shown FIG. 9 by using the pieces of first light L1 and L2 directly incident on the lens portion 165 from the light emitting module 130 at the first incidence angles R1 and R2 and the pieces of light L3 and L4 reflected by the side surface 116 of the recess 111 and emitted to the incidence portion 161, having the second incidence angles R3 and R4.

Figure 7:
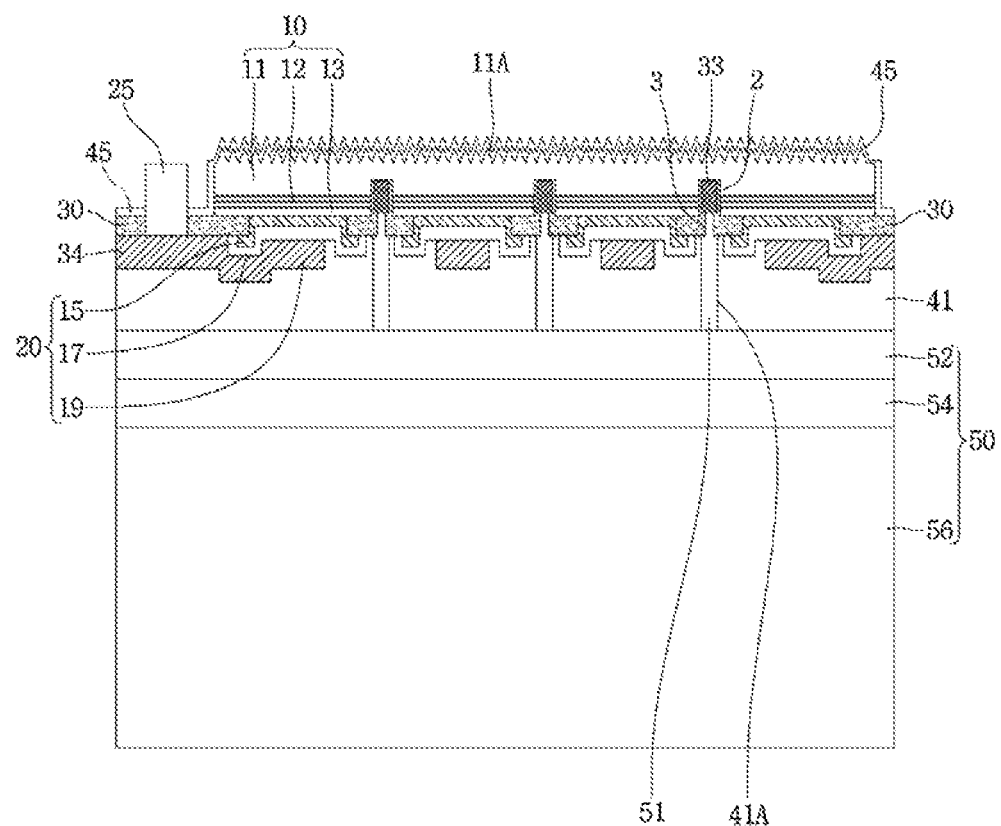
FIG. 7 is a detailed configuration diagram of a light emitting diode of an optical module according to an embodiment.

FIG. 7 is a view illustrating another example of a light emitting diode according to an embodiment.

Referring to FIG. 7, the light emitting diode may include a light emitting structure 10 including a plurality of semiconductor layers 11, 12 and 13, a first electrode layer 20 under the light emitting structure 10, a second electrode layer 50 under the first electrode layer 20, an insulation layer 41 between the first and second electrode layers 20 and 50, and a pad 25.

The light emitting structure 10 may include a first semiconductor layer 11, an active layer 12, and a second semiconductor layer 13. The active layer 12 may be disposed between the first semiconductor layer 11 and the second semiconductor layer 13. The active layer 12 may be disposed under the first semiconductor layer 11, and the second semiconductor layer 13 may be disposed under the active layer 12.

For example, the first semiconductor layer 11 may include an n-type semiconductor layer to which a first conductive type dopant, e.g., an n-type dopant is added, and the second semiconductor layer 13 may include a p-type semiconductor layer to which a second conductive type dopant, e.g., a p-type dopant is added. On the other hand, the first semiconductor layer 11 may be provided as a p-type semiconductor layer, and the second semiconductor layer 13 may be provided as an n-type semiconductor layer.

The light emitting structure 10 is selectively formed of a compound semiconductor of group II to V elements and group III to V elements and is capable of emitting a predetermined peak wavelength within a wavelength range from the ultraviolet band to the visible light band, For example, ultraviolet light can be emitted. The light emitting structure 10 may include the first semiconductor layer 11, the second semiconductor layer 13, and the active layer 12 between the first and second semiconductor layers 11 and 13. Other semiconductor layer may be disposed at least one of the layers 11, 12, and 13, but the invention is not limited thereto.

The first semiconductor layer 11 includes a compositional formula of $In_xAl_yGa_{1-x-y}N$ ($0 \leq x \leq 1$, $0 \leq y \leq 1$, $0 \leq 1\ x+y \leq 1$). The first semiconductor layer 11 may be realized with at least one of a group II-VI compound semiconductor and a group III-V compound semiconductor. For instance, the first semiconductor layer 11 may be selected from the group consisting of GaN, AlN, AlGaN, InGaN, InN, InAlGaN, AlInN, AlGaAs, GaP, GaAs, GaAsP, and AlGaInP. The first conductive dopant includes an n type dopant such as Si, Ge, Sn, Se, or Te.

The active layer 12 may be disposed under the first semiconductor layer 11 and may have at least one of a single quantum well structure, a multiple quantum well (MQW) structure, a quantum dot structure, or a quantum wire structure, but the embodiment is not limited thereto. The active layer 12 includes a pair of a well layer and a barrier layer. The pair of the well layer and the barrier layer, for example, includes at least one pairs of InGaN/GaN, GaN/AlGaN, AlGaN/AlGaN, InGaN/AlGaN, InGaN/InGaN, AlGaAs/GaA, InGaAs/GaAs, InGaP/GaP, AlInGaP/InGaP, and InP/GaAs.

The second semiconductor layer 13 may be disposed under the active layer 12. The second semiconductor layer 13 includes a semiconductor with a second conductive type dopant, for example, a compositional formula of $In_xAl_yGa_{1-x-y}N$ ($0 \leq x \leq 1$, $0 \leq y \leq 1$, $0 < x+y \leq 1$). The second semiconductor layer 13 may be selected from the group consisting of GaN, AlN, AlGaN, InGaN, InN, InAlGaN, AlInN, AlGaAs, GaP, GaAs, GaAsP, and AlGaInP. The second semiconductor layer 13 is a p-type semiconductor layer with a p-type dopant such as Mg, Zn, Ca, Sr, or Ba.

A rough unevenness 11A may be disposed on a top surface of the first semiconductor layer 11, and the unevenness surface 11A may improve light extraction efficiency. The unevenness surface 11A may have a lateral cross-section with a polygonal shape or a hemispherical shape.

The first electrode layer 20 is disposed between the light emitting structure and the second electrode layer 50 and electrically connected to the second semiconductor layer 13 of the light emitting structure 10 and also electrically connected to the second electrode layer 50. The first electrode layer 20 includes a first contact layer 15, a reflective layer 17, and a capping layer 19. The first contact layer 15 is disposed between the reflective layer 17 and the second semiconductor layer 13, and the reflective layer 17 is disposed between the first contact layer 15 and the capping layer 19. The first contact layer 15, the reflective layer 17, and the capping layer 19 may be made of different conductive materials, but is not limited thereto.

The first contact layer 15 may come into contact with the second semiconductor layer, for example, come into ohmic-contact with the second semiconductor layer 13. The first contact layer 15 may be made of, for example, a conductive oxide film, conductive nitride, or a metal. The first contact layer 15 may be made of at least one of indium tin oxide (ITO), ITO nitride (ITON), indium zinc oxide (IZO), IZO nitride (IZON), aluminum zinc oxide (AZO), aluminum gallium zinc oxide (AGZO), indium zinc tin oxide (IZTO), indium aluminum zinc oxide (IAZO), indium gallium zinc oxide (IGZO), indium gallium tin oxide (IGTO), antimony tin oxide (ATO), gallium zinc oxide (GZO), IZO nitride (IZON), ZnO, IrOx, RuOx, NiO, Pt, Ag, and Ti.

The reflective layer 17 may be electrically connected to the first contact layer 15 and the capping layer 19. The reflective layer 17 may reflect light incident from the light emitting structure 10 to perform a function for increasing an amount of light extracted to the outside.

The reflective layer 17 may be made of a metal having light reflectivity of 70% or more. For example, the reflective layer 17 may be made of a metal including at least one of Ag, Ni, Al, Rh, Pd, Ir, Ru, Mg, Zn, Pt, Au and Hf or an ally thereof. Also, the reflective layer 17 may be realized as a multi-layer using the above-described metal or an alloy and a light transmissive conductive material such as indium-tin-oxide (ITO), indium-zinc-oxide (IZO), indium-zinc-tin-oxide (IZTO), indium-aluminum-zinc-oxide (IAZO), indium-gallium-zinc-oxide (IGZO), indium-gallium-tin-oxide (IGTO), aluminum-zinc-oxide (AZO), or antimony-tin-oxide (ATO).

For example, the reflective layer 17 according to an embodiment may include at least one of Ag, Al, an Ag-Pd-Cu alloy, or an Ag-Cu alloy. For example, the reflective layer 17 may have a structure in which an Ag layer and a Ni layer are alternately disposed or may include an Ni/Ag/Ni or Ti layer and a Pt layer. For another example, the first contact layer 15 may be disposed under the reflective layer 17, and at least a portion of the first contact layer 15 may pass through the reflective layer 17 to come into contact with the second semiconductor layer 13. For another example, the reflective layer 17 may be disposed under the first contact layer 15, and a portion of the reflective layer 17 may pass through the first contact layer 15 to come into contact with the second semiconductor layer 13.

The light emitting diode according to an embodiment may include a capping layer 19 disposed under the reflective layer 17. The capping layer 19 comes into contact with a bottom surface of the reflective layer 17, and a contact portion 34 is coupled to a pad 25 to function as a line layer for transmitting power supplied to the pad 25. The capping layer may be made of a metal, for example, at least one of Au, Cu, Ni, Ti, Ti-W, Cr, W, Pt, V, Fe, and Mo.

The contact portion 34 of the capping layer 19 is disposed in a region, which does not vertically overlap the light emitting structure 10, to vertically overlap the pad 25. The contact portion 34 of the capping layer 19 is disposed in a region which does not vertically overlap the first contact layer 15 and the reflective layer 17. The contact portion 34 of the capping layer 19 is disposed at a position lower than that of the light emitting structure 10 to come into direct contact with the pad 25.

The pad 25 may be provided as a single layer or multi-layered structure. The single layer may be made of Au, and when the pad 25 is provided as the multilayered structure, the pad 25 may include at least two materials of Ti, Ag, Cu, and Au. Here, in case of the multilayered structure, a laminated structure of Ti/Ag/Cu/Au or a laminated structure of Ti/Cu/Au may be provided. At least one of the reflective layer 17 and the first contact layer 15 may come into direct contact with the pad 25, but is not limited thereto.

The pad 25 may be disposed at a region between an outer wall of the first electrode layer 20 and the light emitting structure 10. The protection layer 30 and the light transmissive layer 45 may come into contact with a periphery of the pad 25.

The protection layer 30 may be disposed on a bottom surface of the light emitting structure 10 to come into contact with a bottom surface of the second semiconductor layer 13 and the first contact layer 15 and also come into contact with the reflective layer 17.

An inner portion, which vertically overlaps the light emitting structure 10, of the protection layer 30 may be disposed to vertically overlap a region of the protrusion 16. An outer portion of the protection layer 30 may extend upward from the contact portion 34 of the capping layer 19 and be disposed to vertically overlap the contact portion 34. The outer portion of the protection layer 30 may come into contact with the pad 25, for example, be disposed on a circumferential surface of the pad 25.

The inner portion of the protection layer 30 may be disposed between the light emitting structure 10 and the first electrode layer 20, and the outer portion may be disposed between the light transmissive layer 45 and the contact portion 34 of the capping layer 45. The outer portion of the protection layer 30 may extend from a side wall of the light emitting structure 10 to an external region A1 to prevent moisture from being permeated.

The protection layer 30 may be defined as a channel layer, a low refractive index material layer, or an isolation layer. The protection layer 30 may be made of an insulation material, e.g., oxide or nitride. For example, the protection layer 30 may be made of at least one material selected from the group consisting of $SiO_2$, $SiO_y$, $Si_3N_4$, $Si_xN_y$, $SiO_xN_y$, $Al_2O_3$, $TiO_2$, and AlN. The protection layer 30 may be made of a transparent material.

The light emitting diode according to an embodiment may include an insulation layer for electrically insulating the first electrode layer 20 from the second electrode layer 50. The insulation layer 41 may be disposed between the first electrode layer 20 and the second electrode layer 50. An upper portion of the insulation layer 41 may come into contact with the protection layer 30. The insulation layer 41 may be made of, for example oxide or nitride. For example, the insulation layer 41 may be made of at least one material selected from the group consisting of $SiO_2$, $Si_xO_y$, $Si_3N_4$, $Si_xN_y$, $SiO_xN_y$, $Al_2O_3$, $TiO_2$, and AlN.

The insulation layer 41 may have, for example, a thickness of 100 nanometers to 2,000 nanometers. When the insulation layer 41 has a thickness of 100 nanometers or less, insulation characteristics may be deteriorated. When the insulation layer 41 has a thickness exceeding 2,000 nanometers, cracking may occur in the post-process. The insulation layer 41 may come into contact with a bottom surface of the first electrode layer 20 and a top surface of the second electrode layer 50 and thus have a thickness greater than that of each of the protection layer 30, the capping layer 19, the contact layer 15, and the reflective layer 17.

The second electrode layer 50 may include a diffusion barrier layer 52 disposed under the insulation layer 41, a bonding layer 54 disposed under the diffusion barrier layer 52, and a conductive support member 56 disposed under the bonding layer 54 and be electrically connected to the first semiconductor layer 11. Also, the second electrode layer 50 may selectively include one or two of the diffusion barrier layer 52, the bonding layer 54, and the conductive support member 56. At least one of the diffusion barrier layer 52 and the bonding layer 54 may be omitted.

The diffusion barrier layer 52 may be made of at least one of Au, Cu, Ni, Ti, Ti-W, Cr, W, Pt, V, Fe, and Mo. The diffusion barrier layer 52 may function as a diffusion barrier between the insulation layer 41 and the bonding layer 54. The diffusion barrier layer 52 may be electrically connected to the bonding layer 54 and the conductive support member 56 and also electrically connected to the first semiconductor layer 11.

The diffusion barrier layer 52 may perform a function for preventing a material contained in the bonding layer 54 from being diffused in a direction of the reflective layer 17 when the bonding layer 54 is manufactured. The diffusion barrier layer 52 may prevent a material such as tin (Sn) contained in the bonding layer 54 from having an influence on the reflective layer 17.

The bonding layer 54 may be made of a barrier metal or bonding metal, for example, at least one of Ti, Au, Sn, Ni, Cr, Ga, In, Bi, Cu, Ag, Nb, Pd, or Ta. The conductive support member 56 may perform a heat dissipation function by supporting the light emitting structure 10 according to an embodiment. The bonding layer 54 may include a seed layer.

The conductive support member 56 may be formed by using a metal or a carrier substrate, for example, a semiconductor substrate (e.g., Si, Ge, GaN, GaAs, ZnO, SiC, and SiGe) into which Ti, Cr, Ni, Al, Pt, Au, W, Cu, Mo, Cu-W or an impurity is injected. The conductive support member 56 may be a layer for supporting the light emitting diode and have a thickness corresponding to 80% of a thickness of the second electrode layer 50, i.e., a thickness of 30 μm or more.

The second contact layer 33 is disposed in the first semiconductor layer 11 to come into contact with the first semiconductor layer 11. A top surface of the second contact layer may be disposed at a position higher than a bottom surface of the first semiconductor layer 11, electrically connected to the first semiconductor layer 11, and insulated from the active layer 12 and the second semiconductor layer 13.

The second electrode 33 may be electrically connected to the second conductive layer 50. The second contact layer 33 may be disposed to pass through the first electrode layer 20, the active layer 12, and the second semiconductor layer 15. The second contact layer 33 may be disposed in a recess 2 defined in the light emitting structure 10 and insulated from the active layer 12 and the second semiconductor layer 15 by the protection layer 30. The second contact layer 33 may be provided in plurality, and the plurality of second contact layers 33 may be spaced apart from each other.

The second contact layer 33 may be connected to a protrusion 51 of the second electrode layer 50, and the protrusion 51 may protrude from the diffusion barrier layer 52. The protrusion 51 may pass through a hole 41A defined in the insulation layer 41 and the protrusion layer 30 and be insulated from the first electrode layer 20.

The second contact layer 33 may be made of at least one of Cr, V, W, Ti, Zn, Ni, Cu, Al, Au, and Mo. For another example, the protrusion 51 may include at least one of the materials forming the diffusion barrier layer 52 and the bonding layer 54, but is not limited thereto. For example, the protrusion 51 may include at least one of Ti, Au, Sn, Ni, Cr, Ga, In, Bi, Cu, Ag, Nb, Pd or Ta.

The pad 25 is electrically connected to the first electrode layer 20 and exposed to the region outside the sidewall of the light emitting structure 10. The pad 25 may be provided in one or plurality. For example, the pad 25 may be made of at least one of Au, Cu, Ni, Ti, Ti-W, Cr, W, Pt, V, Fe, and Mo.

The light transmissive layer 45 may protect a surface of the light emitting structure 10, insulate the pad 25 from the light emitting structure 10, and come into contact with a peripheral portion of the protection layer 30. The light transmissive layer 45 may have a refractive index less than that of the semiconductor layer constituting the light emitting structure 10 to improve the light extraction efficiency. The light transmissive layer 45 may be made of, for example, oxide or nitride. For example, the light transmissive layer 45 may be made of at least one material selected from the group consisting of $SiO_2$, $SiO_y$, $Si_3N_4$, $SiN_y$, $SiO_xN_y$, $Al_2O_3$, $TiO_2$, and AlN. The light transmissive layer 45 may be omitted according to a design. According to an embodiment, the light emitting structure 10 may be driven by the first electrode layer 20 and the second electrode layer 50.

Figure 8:
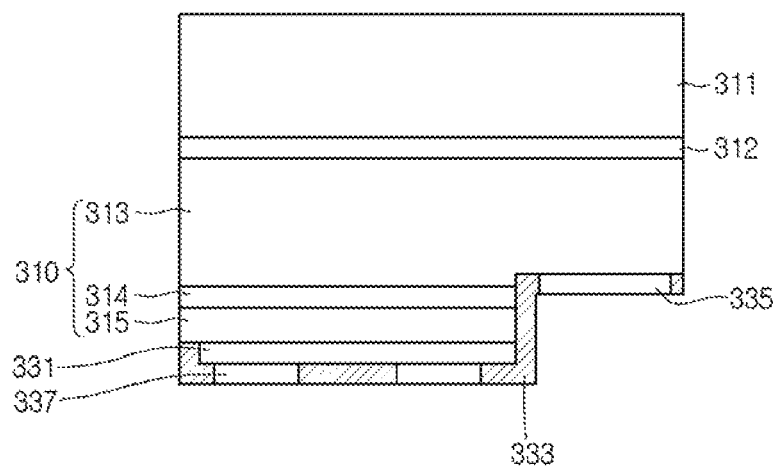
FIG. 8 is another configuration diagram of a light emitting diode of an optical module according to an embodiment.

FIG. 8 is another example of the light emitting diode according to the embodiment.

Referring to FIG. 8, the light emitting diode includes a substrate 311, a first semiconductor layer 312, a light emitting structure 310, an electrode layer 331, an insulating layer 333, a first electrode 335, and a second electrode 337.

The substrate 311 may be, for example, a light transmissive or insulation substrate or a conductive substrate. The substrate 311 may include, for example, at least one of sapphire (Al2O3), SiC, Si, GaAs, GaN, ZnO, Si, GaP, InP, Ge, and Ga2O3. A plurality of convex portions (not shown) may be disposed on a top surface of the substrate 311 to improve light extraction efficiency. Here, the substrate 311 may be removed and the first semiconductor layer 312 or a first conductive semiconductor layer 313 may be disposed in a top layer.

The first semiconductor layer 312 is disposed under the substrate 311. The first semiconductor layer 312 may be formed using a compound semiconductor of Group II to Group V elements. The first semiconductor layer 312 may include at least one of, for example, GaN, InN, AlN, InGaN, AlGaN, InAlGaN, AlInN, AlGaAs, GaP, GaAs, GaAsP, AlGaInP, and GaP. The first semiconductor layer 312 may be formed of at least one of a buffer layer and an undoped (undoped) semiconductor layer, the buffer layer may reduce a difference in lattice constant between the substrate and the nitride semiconductor layer, and the undoped semiconductor layer may be improved quality of the semiconductor crystal. Here, the first semiconductor layer 312 may not be formed.

The light emitting structure 310 is disposed under the first semiconductor layer 312 or the substrate 311. The light emitting structure 310 may be selectively formed of a compound semiconductor of group II to V elements and group III-V elements and is capable of emitting a predetermined peak wavelength within a wavelength range from the ultraviolet band to the visible light band.

The light emitting structure 310 includes a first conductive semiconductor layer 313, a second conductive semiconductor layer 315, and an active layer 314 between the first and second semiconductor layers 313 and 315. The first and second semiconductor layers 313 and 315 may formed of structure of a single layer or multi-layer.

The first conductive semiconductor layer 313 may include a semiconductor layer doped with a first conductive dopant, for example, an n-type semiconductor layer. The first conductive semiconductor layer 313 includes a composition formula of $In_xAl_yGa_{1-x-y}N$ ($0 \leq x \leq 1$, $0 \leq y \leq 1$, $0 \leq x+y \leq 1$). The first conductive semiconductor layer 313 may be a compound semiconductor of Group III-V elements such as GaN, AlN, AlGaN, InGaN, InN, InAlGaN, AlInN, AlGaAs, GaP, GaAs, and GaAsP. The first conductive dopant is an n-type dopant and includes dopants such as Si, Ge, Sn, Se, and Te.

The active layer 314 is disposed under the first conductive semiconductor layer 313 and selectively includes a single quantum well, a multiple quantum well (MQW), a quantum wire structure, or a quantum dot structure. The active layer 314 includes a pair of a well layer and a barrier layer. The pair of the well layer and the barrier layer, for example, includes at least one pairs of InGaN/GaN, GaN/AlGaN, AlGaN/AlGaN, InGaN/AlGaN, InGaN/InGaN, AlGaAs/GaA, InGaAs/GaAs, InGaP/GaP, AlInGaP/InGaP, and InP/GaAs.

The second semiconductor layer 315 may be disposed under the active layer 314. The second semiconductor layer 315 includes a semiconductor with a second conductive type dopant, for example, a compositional formula of $In_xAl_yGa_{1-x-y}N$ ($0 \leq x \leq 1$, $0 \leq y \leq 1$, $0 \leq x+y \leq 1$). The second semiconductor layer 315 may be selected from the group consisting of GaN, AlN, AlGaN, InGaN, InN, InAlGaN, AlInN, AlGaAs, GaP, GaAs, GaAsP, and AlGaInP. The second semiconductor layer 13 is a p-type semiconductor layer with a p-type dopant such as Mg, Zn, Ca, Sr, or Ba.

The light emitting structure 310 is another example, the first conductive semiconductor layer 313 may be a p-type semiconductor layer, and the second conductive semiconductor layer 315 may be an n-type semiconductor layer. A third conductive type semiconductor layer having a polarity opposite to the second conductive type may be formed under the second conductive semiconductor layer 315. Also, the light emitting structure 310 may have any one of an n-p junction structure, a p-n junction structure, an n-p-n junction structure, and a p-n-p junction structure.

The electrode layer 331 is formed under the conductive semiconductor layer 315. The electrode layer 331 includes a reflective layer, the reflective layer may further include an ohmic contact with the light emitting structure 310. The reflective layer may be selected from a reflectance of 70% or more materials, for example, a metal of Al, Ag, Ru, Pd, Rh, Pt, and Ir and an alloy of two or more of the above metals. The electrode layer 331 may include a stack structure of the transparent electrode layer/reflective layer, for example comprising a single-layer or multi-layer structure. The surface of at least one layer of conductive semiconductor layer 315 and the electrode layer 331 has a light extracting structure such as a roughness may be formed, such a light extracting structure is given by changing the light critical angle of incident, and improves light extraction efficiency. The light reflected by the electrode layer 331 may be emitted through the substrate 311.

A first electrode is disposed under a portion of the first conductive semiconductor layer 313 and a second electrode 337 is disposed under a portion of the electrode layer 331.

The first electrode 335 is electrically connected to the first conductive semiconductor layer 315, and the second electrode 337 is electrically connected to the second conductive semiconductor layer 315 through the electrode layer 331. The first electrode 335 and the second electrode 337 may formed of at least one or an alloy of Cr, Ti, Co, Ni, V, Hf, Ag, Al, Ru, Rh, Pt, Pd, Ta, Mo, and W. The first and second electrodes 335 and 337 may be the same, or a laminated structure formed of a different laminated structure, and may be a single layer or multi-layer structure.

The insulating layer 333 may disposed under the electrode layer 331 and is disposed on a lower surface of the second conductive semiconductor layer 315, a side surfaces of the second conductive semiconductor layer 315 and the active layer 314, and a portion region of the first conductor semiconductor layer 313. The insulating layer 333 is disposed on an excluding region of the electrode layer 331, the first electrode 335, and the second electrode 337, and is electrically protected a lower portion electrical of the light emitting structure 310. The insulating layer 333 comprises an insulating material or an insulating resin formed of at least one of an oxide, a nitride, a fluoride, and sulfide materials having Al, Cr, Si, Ti, Zn, and Zr. The insulating layer 333 is, for example, SiO2, may be selectively formed from Si3N4, Al2O3, and TiO2. The insulating layer 333 is to form a metal structure for a flip-bonded under the light emitting structure 310 is formed to prevent the interlayer short of the light emitting structure 310.

Embodiment may be disposed a phosphor layer (not shown) on the light emitting diode, and the phosphor layer may be disposed on an upper surface of a light emitting diode, or an upper/side surfaces of the light emitting diode. The phosphor layer can be improved is the wavelength of the light emitted from the conversion efficiency of the LED. The phosphor layer may include at least one of a red phosphor, a green phosphor, a blue phosphor, a yellow phosphor, but is not limited thereto. The phosphor may be selectively formed from e.g., YAG, TAG, Silicate, Nitride, Oxy-nitride-based material.

Optical module according to an embodiment may be provided as a unit or may be provided in a form that is arranged in a plurality of optical modules. The optical module according to the embodiment can be applied to the UV lamp of the exposure system or a curing machine.

Features, structures, and effects described in the above embodiments are incorporated into at least one embodiment, but are not limited to only one embodiment. Moreover, features, structures, and effects exemplified in one embodiment can easily be combined and modified for another embodiment by those skilled in the art. Therefore, these combinations and modifications should be construed as falling within the scope of the present invention.

INDUSTRIAL APPLICABILITY

The present invention may provide an ultraviolet optical module.

The present invention provides an ultraviolet optical module having a narrow beam spread angle and may be applied to industrial and industrial lamps.

The present invention can be applied as a lamp of an exposure machine or a hardening machine with an ultraviolet module having a narrow beam spread angle.

The invention claimed is:

1. An optical module comprising:
   a body including an upper surface, a lower surface opposite to the upper surface, and a concave recess toward the lower surface from the upper surface of the body;
   a light emitting module including a light emitting diode under the recess of the body; and
   an optical lens including an incidence portion having an incidence surface on the body and a lens portion having a curved surface that protrudes convexly from the incidence portion,
   wherein the incidence portion is disposed on the upper surface of the body and the recess,
   the incidence portion includes a first region overlapped with the upper surface of the body in a vertical direction and a second region overlapped with an upper portion of the recess in the vertical direction along an outer periphery of the lens portion,
   wherein the second region is disposed between the first region and a region overlapped with the lens portion in the vertical direction,
   the lens portion overlaps with the recess in the vertical direction,
   the upper portion of the recess has a maximum first diameter,
   a lower portion of the lens portion has a maximum second diameter,
   the second diameter is smaller than the first diameter,
   wherein a lower portion of the recess has a third diameter smaller than the second diameter,
   wherein the body includes a receiving portion through which the lower portion of the recess and the lower surface of the body penetrate vertically; and a side surface having a curvature around the recess,
   wherein a side wall of the receiving portion includes a stepped structure extending from the side surfaces of the recess toward a bottom of the receiving portion,
   wherein a width of the receiving portion is equal to the third diameter,
   wherein the light emitting module is disposed in the receiving portion,
   wherein an upper surface of the light emitting diode is disposed lower than a horizontal straight line connecting a lower end of curved surface of the recess, and
   wherein a depth of the recess is greater than a height of the receiving portion.

2. The optical module of claim 1,
   wherein the light emitting module includes a circuit board disposed on the bottom of the receiving portion,
   wherein the light emitting diode is disposed on the circuit board and is electrically connected to the circuit board, and
   wherein a width of the circuit board is smaller than the width of the receiving portion.

3. The optical module of claim 1, wherein the lens portion includes an aspherical shape, and
   an area of a lower surface of the second region in the incidence portion is smaller than that of a lower surface of the first region.

4. The optical module of claim 3, wherein a height of the optical lens is smaller than the depth of the recess,
   a ratio of the first diameter and the second diameter is in a range of 1: 0.81 to 1: 0.91, and
   the incidence portion of the optical lens has a flat incidence surface, and a beam spread angle of light emitted from the optical lens is 15 degrees or less.

5. The optical module of claim 1,
   a bottom center of the receiving portion is aligned with a center of the lens portion,
   wherein first light emitted from the light emitting diode is directly incident on the lens portion at a first incidence angle with respect to an optical axis and is emitted at a first exit angle through the lens portion, and
   second light emitted from the light emitting diode is reflected at the side surface of the recess at a second incidence angle with respect to the optical axis and is emitted at a second exit angle through the incidence portion disposed at an outside of the lens portion,
   wherein the first incidence angle is 35 degrees or less with respect to the optical axis, the second incidence angle is greater than 35 degrees with respect to the optical axis, and the first and second exit angles include 15 degrees or less with respect to the optical axis or a vertical axis.

6. The optical module of claim 1, wherein first light emitted from the light emitting diode is directly incident on the lens portion at a first incidence angle with respect to an optical axis and is emitted at a first exit angle through the lens portion, and
   second light emitted from the light emitting diode is reflected at the side surface of the recess at a second incidence angle with respect to the optical axis and is emitted at a second exit angle through the incidence portion disposed at an outside of the lens portion,
   wherein a ratio of the first incidence angle and the first exit angle is 1.7 or less, and
   a ratio of the second incidence angle and the second exit angle is 0.375 or less.

7. The optical module of claim 1, wherein the body includes a ceramic material or an aluminum material,
   the recess has a circular shape in top view, and
   a diameter of the recess gradually decreases toward the light emitting diode.

8. The optical module of claim 1, wherein the curved side surface of the recess has a radius of curvature of 1.5 mm or less, wherein a lower surface of the incidence portion includes a flat horizontal surface, and an area of the lower surface of the incidence portion is larger than that of an upper surface of the recess.

9. The optical module of claim 1, wherein the light emitting diode emits light of an ultraviolet wavelength, the recess has a circular shape in top view, a diameter of the recess gradually decreases toward the light emitting diode, and a beam spread angle of light emitted from the optical lens is 15 degrees or less.

10. The optical module of claim 2, wherein the light emitting diode emits light of an ultraviolet wavelength, a lower surface of the circuit board is disposed in a same horizontal plane, and the circuit board includes a ceramic material.

11. The optical module of claim 1, wherein the second diameter is less than the first diameter and is 80% or more of the first diameter.

12. An optical module comprising:

a body including an upper surface, a lower surface opposite to the upper surface, a recess a concave recess toward the lower surface from the upper surface of the body, and a receiving portion under the recess;

a light emitting module including a circuit board on a bottom of the receiving portion and a light emitting diode on the circuit board; and an optical lens including an incidence portion having an incidence surface on the body and a lens portion having a curved surface that protrudes convexly from the incidence portion, wherein the incidence portion is disposed on the upper surface of the body and on the recess, wherein the lens portion overlaps the recess in a vertical direction, wherein the upper portion of the recess has a maximum first diameter, wherein a lower portion of the lens portion has a maximum second diameter, the second diameter is smaller than the first diameter, the lower portion of the recess has a third diameter smaller than the second diameter, wherein the receiving portion is vertically penetrated with a lower portion of the recess and the lower surface of the body, wherein the recess includes a side surface having a curvature around thereof, wherein a side wall of the receiving portion extends vertically from a lower end of the side surface of the recess toward the bottom of the receiving portion, wherein the light emitting module is disposed in the receiving portion, wherein a width of the receiving portion is equal to the third diameter, wherein the light emitting module is disposed in the receiving portion, wherein an upper surface of the light emitting diode is disposed lower than a horizontal straight line connecting a lower end of the side surface of the recess, wherein a depth of the recess is greater than a height of the receiving portion, and wherein a height of the receiving portion is greater than a thickness of the light emitting module.

13. The optical module of claim 12, wherein the incidence portion includes a first region overlapped with the upper surface of the body in a vertical direction and a second region overlapped with an upper portion of the recess in the vertical direction along an outer periphery of the lens portion, wherein the second region is disposed between the first region and an region overlapped with the lens portion in the vertical direction, and wherein the second diameter is 80% or more of the first diameter.

14. The optical module of claim 13, wherein the light emitting diode emits a wavelength in the range of 100 nm to 400 nm, wherein a diameter of the recess gradually decreases toward the light emitting diode, and wherein the body comprises a ceramic material or an aluminum material.

15. The optical module of claim 13, wherein the circuit board is electrically connected to the light emitting diode, and wherein an interval between the light emitting diode and the side wall of the receiving portion is less than 0.5 mm.

16. The optical module of claim 13, wherein the depth of the recess is greater than a height of the optical lens, wherein the optical lens comprises a thickness less than a thickness of the body, and wherein a thickness of the incidence portion is 30% or less of the thickness of the optical lens.

17. The optical module of claim 13, wherein the second diameter is less than 6 mm, and wherein a ratio of the first diameter to the second diameter is in a range of 1: 0.81 to 1: 0.91.

18. The optical module of claim 13, wherein a lower diameter of the recess is a third diameter, wherein a diameter at a half of the height of the recess is a fourth diameter, wherein the third diameter being smaller than the first diameter and greater than the third diameter, and wherein the fourth diameter is less than the second diameter.

19. The optical module of claim 13, wherein a bottom center of the light emitting diode and the peak point of the lens portion of the optical lens are aligned on an optical axis, wherein a straight line connecting a bottom center of the light emitting diode and an upper end of the side surface of the recess is disposed at a first angle with respect to the optical axis, wherein a straight line connecting a bottom center of the light emitting diode and an outer lower point of the lens portion of the optical lens is disposed at a second angle with respect to the optical axis, wherein the second angle is larger than the first angle, and wherein a difference between the first and second angles is in a range of 7.3±0.7 degrees.

20. The optical module of claim 19, wherein the first angle is 35 degrees or less, wherein a straight line connecting the peak point of the optical lens and the outer lower point of the lens portion is disposed at a third angle with respect to the optical axis, wherein a straight line connecting the highest point of the optical lens and the upper end of the side surface of the recess is disposed at a fourth angle with respect to the optical axis, wherein the third angle is greater than the fourth angle, wherein a difference between the third and fourth angles is in a range of 2 degrees to 4 degrees, and wherein a ratio of a radius of the first diameter to a radius of the lens portion is in a range of 1: 0.81 to 1: 0.91.

* * * * *